United States Patent [19]
Kim et al.

[11] Patent Number: 5,650,412
[45] Date of Patent: Jul. 22, 1997

[54] HIV PROTEASE INHIBITORS USEFUL FOR THE TREATMENT OF AIDS

[75] Inventors: Byeong Moon Kim, Hatfield; Joseph P. Vacca, Telford, both of Pa.

[73] Assignee: Merck & Co., Inc., Rahway, N.J.

[21] Appl. No.: 548,415

[22] Filed: Oct. 26, 1995

Related U.S. Application Data

[63] Continuation of Ser. No. 289,477, Aug. 11, 1994, abandoned.

[51] Int. Cl.$^6$ .................. A61K 31/495; C07D 409/14
[52] U.S. Cl. .................. 514/253; 544/362; 544/363; 544/373; 544/374; 544/376; 544/377; 544/387; 544/388; 546/114; 546/115; 549/62; 549/517; 549/527; 549/552; 514/43; 514/49; 514/220; 514/230.5; 514/252
[58] Field of Search ..................... 544/377; 514/253

[56] References Cited

FOREIGN PATENT DOCUMENTS

| | | |
|---|---|---|
| 0346847 | 12/1989 | European Pat. Off. |
| 0486948 | 5/1992 | European Pat. Off. |
| 0541168 | 5/1993 | European Pat. Off. |
| WO92/08698 | 5/1992 | WIPO |
| WO92/08700 | 5/1992 | WIPO |

OTHER PUBLICATIONS

Bigge, et al., "New Preparations of the N-Methyl-D-Aspartate Receptor Antagonist, 4-(3-phosphonopropyl)-2-...", Tet. Lett., vol. 30, No. 39, pp. 5193–5196, 1989.
Caron, et al., "Radioselective Azide Opening of 2,3-Epoxy Alcohols by [Ti(O-i-Pr)2(N3)2]: Synthesis ...", J. Org., Chem., 53, pp. 5185–5187, 1988.
Cohen, et al., "Characterization of the Binding Site for Nevirapine (BI-RG-587), a Nonnucleoside Inhibitor ...", J. Biol. Chem., vol. 266, No. 22, pp. 14670–14674, 1991.
Felder, et al., "Uber die Katalytische Hydrierung Von Pyrazincarbonsauren", Helv. Chim. Acta, 43(117), pp. 888–896, 1960.
Gao, et al., "Catalytic Asymmetric Epoxidation and Kinetic Resolution: Modified Procedures Including in Situ Derivatization", J. Am. Chem. Soc., 109, pp. 5765–5780, 1987.
Hargrave, et al., "Novel Non-Nucleoside InhibitorsIV-1 Reverse Transcriptase. 1. Tricyclic Pyridobenzo— and Dipyridodiazepinones", J. Med. Chem., vol. 34, pp. 2231–2241, 1991.
Klunder, et al., "Novel Non-Nucleotide Inhibitors of HIV-1 Reverse Transcriptase. 2. Tricyclic Pyridobenzoxazapinones and Dibenzaxazapinones", J. Chem., vol.34, pp. 2231–2241, 1991.
Winslow et al, AIDS, 8 pp. 753–756 (1994).
Kageyama et al, Antimicrobial Agents and Chemotherapy 36, pp. 926–933 (1992).

Primary Examiner—Emily Bernhardt
Attorney, Agent, or Firm—Mary A. Appollina; Melvin Winokur; Paul D. Matukaitis

[57] ABSTRACT

Compounds of formula

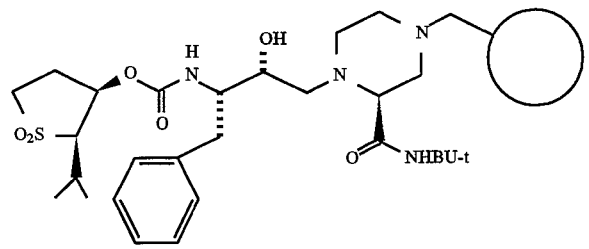

are HIV protease inhibitors. These compounds are useful in the prevention or treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

6 Claims, No Drawings

HIV PROTEASE INHIBITORS USEFUL FOR THE TREATMENT OF AIDS

This is a continuation of application Ser. No. 08/289,477 filed Aug. 11, 1994, now abandoned.

The present invention is concerned with compounds which inhibit the protease encoded by human immunodeficiency virus (HIV) or pharmaceutically acceptable salts thereof and are of value in the prevention of infection by HIV, the treatment of infection by HIV and the treatment of the resulting acquired immune deficiency syndrome (AIDS). It also relates to pharmaceutical compositions containing the compounds and to a method of use of the present compounds and other agents for the treatment of AIDS and viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.* 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313,277 (1985)]. Amino acid sequence homology provides evidence that the pol sequence encodes reverse transcriptase, an endonuclease and an HIV protease [Toh, H. et al., *EMBO J.* 4, 1267 (1985); Power, M. D. et al., *Science*, 231, 1567 (1986); Pearl, L. H. et al., *Nature* 329, 351 (1987)]. Applicants demonstrate that the compounds of this invention are inhibitors of HIV protease. Compounds of this invention are active against HIV protease resistant to other HIV protease inhibitors.

BRIEF DESCRIPTION OF THE INVENTION

Compounds of Formula I, as herein defined, are disclosed. These compounds are useful in the inhibition of HIV protease, the prevention of infection by HIV, the treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS, methods of preventing infection by HIV, and methods of treating infection by HIV are also disclosed.

Some abbreviations that may appear in this application are as follows.

ABBREVIATIONS

| Designation | |
|---|---|
| | Protecting Group |
| BOC (Boc) | t-butyloxycarbonyl |
| CBZ (Cbz) | benzyloxycarbonyl (carbobenzoxy) |
| TBS (TBDMS) | t-butyl-dimethylsilyl |
| | Activating Group |
| HBT (HOBT or HOBt) | 1-hydroxybenzotriazole hydrate |
| | Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chloride |
| EDC | 1-ethyl-3-(3-dimethylaminopropyl) carbodiimide hydrochloride |
| | Other |
| (BOC)$_2$O (BOC$_2$O) | di-t-butyl dicarbonate |
| n-Bu$_4$N+F— | tetrabutyl ammonium fluoride |
| nBuLi (n-Buli) | n-butyllithium |
| DMF | dimethylformamide |
| Et$_3$N | triethylamine |
| EtOAc | ethyl acetate |
| TFA | trifluoroacetic acid |
| DMAP | dimethylaminopyridine |
| DME | dimethoxyethane |
| LDA | lithium diisopropylamide |
| THF | tetrahydrofuran |
| | Amino Acid |
| Ile | L-isoleucine |
| Val | L-valine |

DETAILED DESCRIPTION OF THE INVENTION AND PREFERRED EMBODIMENTS

This invention is concerned with compounds of Formula I, combinations thereof, or pharmaceutically acceptable salts thereof, in the inhibition of HIV protease, the prevention or treatment of infection by HIV and in the treatment of the resulting acquired immune deficiency syndrome (AIDS). Compounds of Formula I are defined as follows:

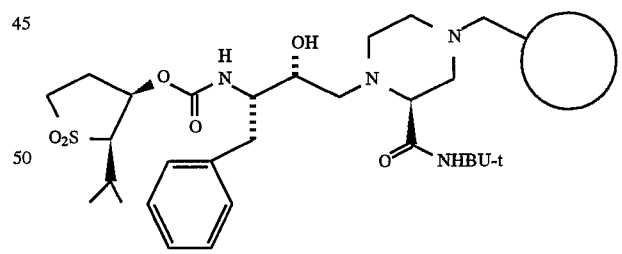

or pharmaceutically acceptable salts thereof, wherein:

is a stable 8- to 10-membered bicyclic heterocycle, any ring of which may be saturated or unsaturated, and which consists of carbon atoms and 1–3 heteroatoms selected from the group consisting of N, S or O, said heterocycle unsubstituted or substituted with OH, halo, $C_{1-4}$ alkyl, $C_{1-4}$ alkoxy, oxo;

with the proviso that

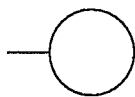

is not

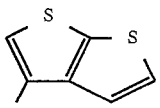

nor

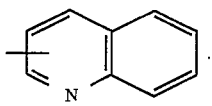

One preferred embodiment of the present invention is compounds of Formula I, or pharmaceutically acceptable salts thereof, wherein:

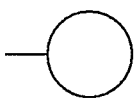

is a stable 8- to 10-membered bicyclic heterocycle, any ring of which may be saturated or unsaturated, and which consists of carbon atoms and 2 heteroatoms selected from the group consisting of N or O, wherein the heteroatoms are in different rings.

A second preferred embodiment are compounds of Formula I wherein:

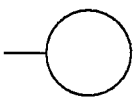

is restricted to

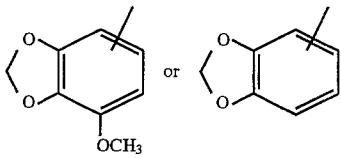

or a pharmaceutically acceptable salt thereof.

A third embodiment are compounds of Formula I wherein:

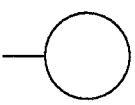

is restricted to

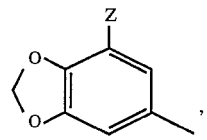

or pharmaceutically acceptable salts thereof

Another preferred embodiment of the present invention is Compound A:

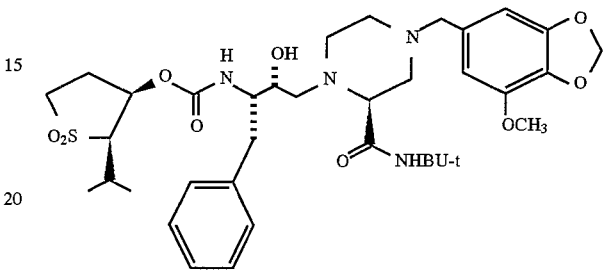

which is N-tert-butyl-1-[2'(R)-hydroxy-4'-phenyl-3'(S)-[3"(R)-[1'",1'"-dioxo-2'"(R)-methylethyl]tetrahydrothienyloxycarbonylamino]butyl]-4-[(3'-methoxy-4',5'-methylenedioxyphenyl)methyl]piperazine-2(S)-carboxamide or pharmaceutically acceptable salt thereof.

The compounds of the present invention, may have asymmetric centers and occur as racemates, racemic mixtures and as individual diastereomers, or enantiomers with all isomeric forms being included in the present invention. A racemate or racemic mixture does not imply a 50:50 mixture of stereoisomers.

When any variable (e.g., )

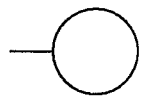

occurs more than one time in any constituent or in Formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents an alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluroacetate, perchlorate, nitrate, benzoate, maleate, tartrate, hemitartrate, benzene sulfonate, and the like.

The term heterocycle or heterocyclic, as used herein except where noted, represents a stable 5to 7-membered mono- or bicyclic or stable 7- to 10-membered bicyclic heterocyclic ting system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

Schemes I–II for preparing the novel compounds of this invention are presented below. The examples specifically illustrate the application of the following schemes to specific compounds.

Amide couplings used to form the compounds of this invention are typically performed by the carbodiimide method with reagents such as dicyclohexylcarbodiimide, or 1-ethyl-3-(3-dimethyl-aminopropyl)carbodiimide. Other methods of forming the amide or peptide bond include, but are not limited to the synthetic routes via an acid chloride, azide, mixed anhydride or activated ester. Typically, solution phase amide coupling are performed, but solid-phase synthesis by classical Merrifield techniques may be employed instead. The addition and removal of one or more protecting groups is also typical practice.

The compounds of the present invention are prepared in accordance with Schemes I–V.

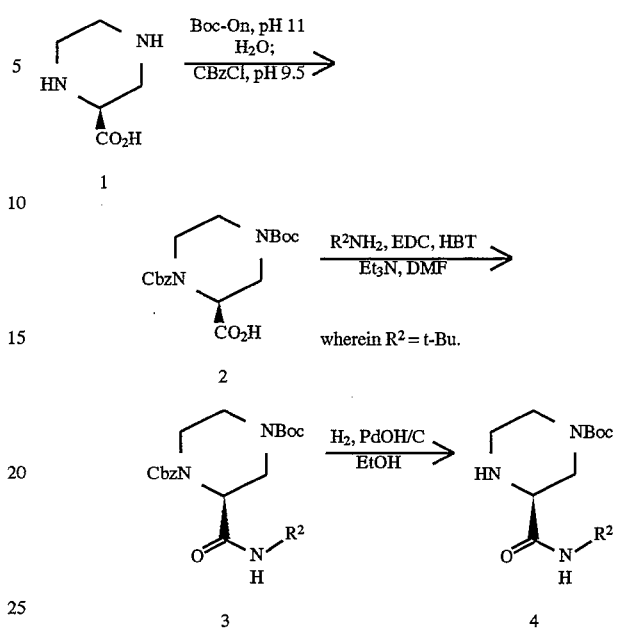

Compound 2 is prepared by the procedure of Bigge, C. F. et al., *Tetrahedron Lett.*, 30, 5193 (1989); starting with 2(S)-piperazine-carboxylic acid. [See also Felder, E. et al., *Helv. Chim. Acta*, 117, 888 (1960)]. Coupling of the acid 2 with t-butylamine under the effect of HOBt and EDC provides the t-butylamide 3, which, upon hydrogenation, is converted to the amine 4. Example 1 illustrates but does not limit Scheme 1.

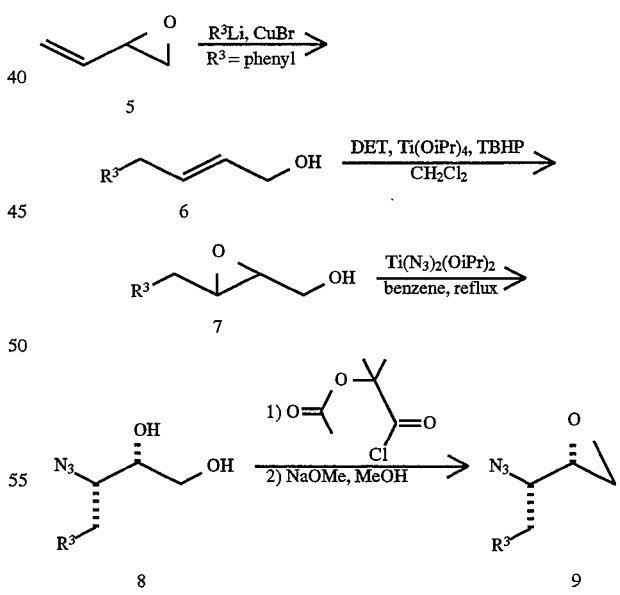

Catalytic asymmetric or Sharpless epoxidation of the allylic alcohol 6 to produce 7 is performed by the methods of Gao, Y. et al., *J. Am. Chem. Soc.* 109, 5765 (1987). Regio-selective azide opening of the 2,3-epoxy alcohol 7 to give 8 is facilitated by titanium according to Caron, M. et al., *J. Org. Chem.* 53, 5185 (1988). Example 2 illustrates but does not limit Scheme II.

SCHEME III

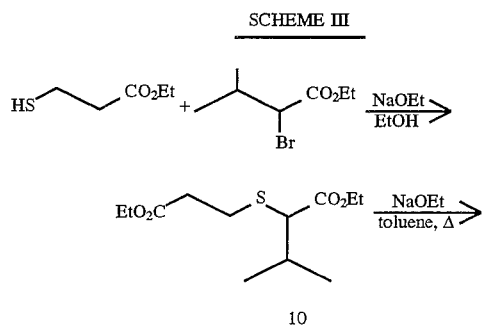

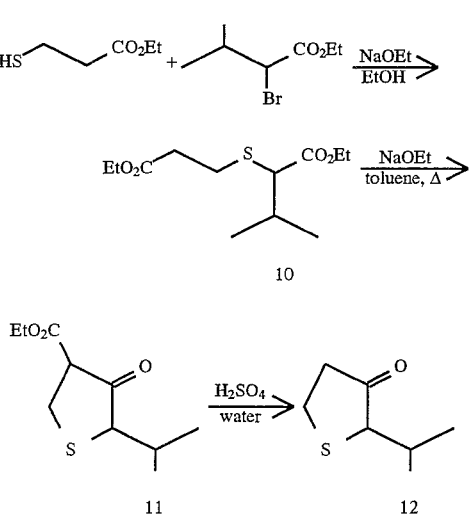

2(R, S), 3(R, S)

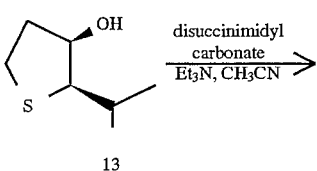

14

2(R, S), 3(R, S)

15  16

The coupling reaction of ethyl 3-mercaptopropionate and ethyl 2-bromo-3-methylbutanoate furnishes Compound 10 which is cyclized under Dieckman conditions to give the keto ester 11. Hydrolytic decarboxylation of 11 by $H_2SO_4$ followed by selective reduction of the ketone 12 yields the alcohol 13 which is converted to the mixed carbonate 14 using disuccinimidyl carbonate in the presence of a base, e.g. triethylamine. Compounds 15 and 16 are made by reacting the corresponding alcohols with disuccinimidyl carbonate. Examples 3–6 illustrate but do not limit Scheme III.

SCHEME IV

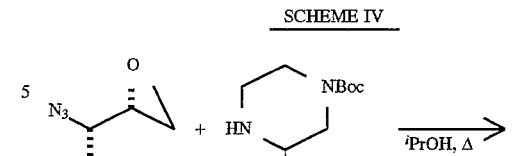

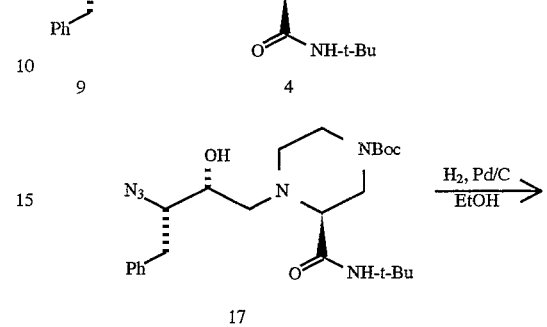

17

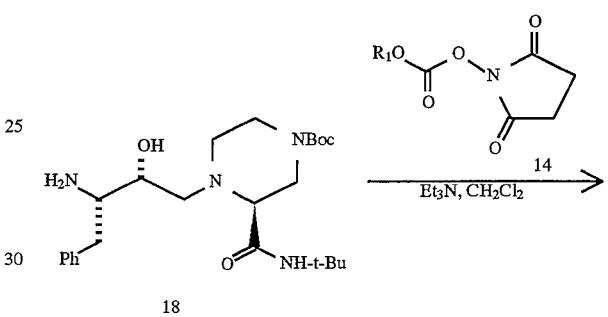

18

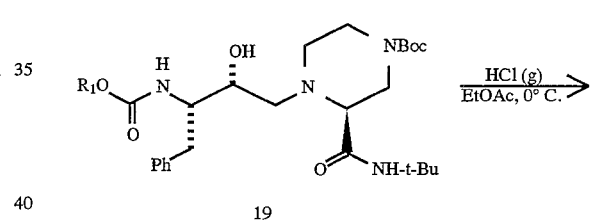

19

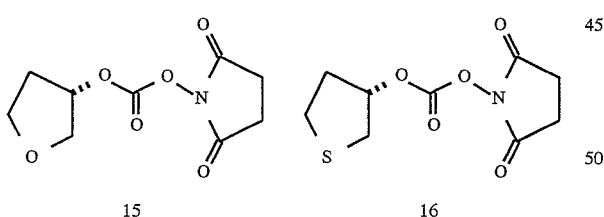

20

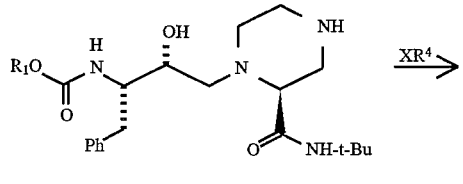

21

Where $R^1 =$ 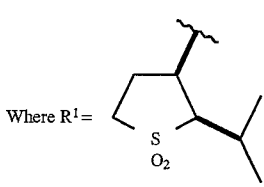

-continued
SCHEME IV

and R⁴ = ⟨shape⟩ as defined above;

Condensation of the azide epoxide 9 with the piperazine intermediate 4 is performed by, for example, heating a mixture in refluxing isopropanol, to give the azido-alcohol 17 in good yield. Reduction over palladium on carbon yields the amine 18, which is then reacted with the appropriate N-substituted succinimide 14 in the presence of, e.g., TEA, to give Compound 19. When coupling with 14, the sulfide groups are selectively oxidized by catalytic amount of $O_sO_4$ and stoichiometric amount of N-methyl-morpholine N-oxide (NMO). Isomers are separated in the case of coupling with 14. Then the protecting Boc group is removed by acid treatment and the subsequent free amine is coupled to the substituents through alkylation, reductive amination, or amidation. Examples 1–2 illustrate but do not limit Scheme IV.

The compounds of this invention are also illustrated by the tables below Example 11.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

The compounds of the present invention are useful in the inhibition of HIV protease the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by HIV is effectively treated by the administration of from 1.0 to 50 milligrams of the compound per kilogram of body weight from one to four times per day. In one preferred regimen, dosages of 100–400 mg every six hours are administered orally to each patient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV protease inhibitory compounds with one or more agents useful in the treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

TABLE C

| Drug Name | Manufacturer | Indication |
|---|---|---|
| ANTIVIRALS | | |
| AL-721 | Ethigen | ARC, PGL |
|  | (Los Angeles, CA) | HIV positive, AIDS |
| Recombinant Human | Triton Biosciences | AIDS, Kaposi's |

TABLE C-continued

| Drug Name | Manufacturer | Indication |
|---|---|---|
| Interferon Beta | (Almeda, CA) | sarcoma, ARC |
| Acemannan | Carrington Labs (Irving, TX) | ARC (See also immunomodulators) |
| Cytovene | Syntex | sight threatening CMV |
| Ganciclovir | (Palo Alto, CA) | peripheral CMV retinitis |
| d4T Didehydrodeoxythymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Trisodium Phosphonoformate | Astra Pharm. Products, Inc. (Westborough, MA) | CMV retinitis, HIV infection, other CMV infections |
| Dideoxycytidine; ddC | Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT AIDS, adv, ARC | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 | Adria Laboratories (Dublin, OH) Erbamont (Stamford, CT) | ARC |
| Dextran Sulfate | Ueno Fine Chem. Ind. Ltd. (Osaka, Japan) | AIDS, ARC, HIV positive asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant Interferon in an immuno-adsorption column | Advanced Biotherapy Concepts (Rockville, MD) | AIDS, ARC |
| B | Merck (Rahway, NJ) | AIDS, ARC, asymptomatic HIV positive, also in combination with AZT. |
| C | Merck (Rahway, NJ) | AIDS, ARC, asymptomatic HIV positive, also in combination with AZT. |
| Nevirapine | Boehringer Ingelheim | AIDS, ARC, asymptomatic HIV positive, also in combination with AZT. |
| J | Merck (Rahway, NJ) | AIDS, ARC, asymptomatic HIV positive, also in combination with AZT. |
| D | Hoffman-La Roche | AIDS, ARC, asymptomatic HIV positive, also in combination with AZT. |
| E | Monsanto | AIDS, ARC, asymptomatic HIV positive, also in combination with AZT. |
| F | Abbott | AIDS, ARC, positive, also in combination with AZT. |

IMMUNO-MODULATORS

| Drug Name | Manufacturer | Indication |
|---|---|---|
| AS-101 | Wyeth-Ayerst Labs. (Philadelphia, PA) | AIDS |
| Bropirimine | Upjohn (Kalamazoo, MI) | advanced AIDS |
| Acemannan | Carrington Labs, Inc. (Irving, TX) | AIDS, ARC (See also anti-virals) |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti-virals) |
| Gamma Interferon | Genentech (S. San Francisco, CA) | ARC, in combination w/TNF (tumor necrosis factor) |
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoeschst-Roussel (Sommerville, NJ) Immunex (Seattle, WA) | AIDS |
| Granulocyte Macrophage Colony Stimulating Factor | Schering-Plough (Madison, NJ) | AIDS |
| HIV Core Particle Immunostimulant | Rorer (Ft. Washington, PA) | AIDS, in combination w/AZT seropositive HIV |
| IL-2 Interleukin-2 | Cetus (Emeryville, CA) | AIDS, in combination w/AZT |
| IL-2 Interleukin-2 | Hoffman-La Roche (Nutley, NJ) Immunex | AIDS, ARC, HIV, in combination w/AZT |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposi's sarcoma W/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |
| Granulocyte Colony Stimulating Factor | Amgen (Thousand Oaks, CA) | AIDS, in combination w/AZT |
| rCD4 Recombinant | Genentech (S. San Francisco, CA) | AIDS, ARC |

TABLE C-continued

| Drug Name | Manufacturer | Indication |
|---|---|---|
| Soluble Human CD4 | | |
| rCD4-IgG hybrids | | AIDS, ARC |
| Recombinant Soluble Human CD4 | Biogen (Cambridge, MA) | AIDS, ARC |
| Interferon Alfa 2a | Hoffman-La Roche (Nutley, NJ) | Kaposi's sarcoma AIDS, ARC, in combination w/AZT |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Fluconazole | Pfizer (New York, NY) | cryptococcal meningitis, candidiasis prevention of |
| Pastille Nystatin Pastille | Squibb Corp. (Princeton, NJ) | prevention of oral candidiasis |
| Ornidyl Eflornithine | Merrell Dow (Cincinnati, OH) | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. w/AIDS |
| Total Enteral Nutrition | Norwich Eaton Pharmaceuticals (Norwich, NY) | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Certain compounds of Table C are the following:

Compound B is 6-chloro-4-(S)-cyclopropyl-3,4dihydro-4-((2-pyridyl)ethynyl)quinazolin-2(1H)-one;

Compound C is (−) 6-chloro-4(S)-trifluoromethyl-1,2-dihydro-4(H)-3,1-benzoxazin-2-one; nevirapine is 11-cyclopropyl-5,11-dihydro-4-methyl-6H-dipyrido[3,2-b:2',3'-e][1,4]diazepin-6-one. Compounds B and C are synthesized by the methods of EP 0569083. Nevirapine is synthesized by Klunder, J. M. et al., *J. Med. Chem.* 35, 1887 (1992); Hargrave, K. D. et al., *J. Med Chem.* 34, 2231 (1991); Cohen, K. A. et al., *J. Biol. Chem.* 266, 14670 (1991).

Other compounds of Table C include the following HIV protease inhibitors.

Compound J is

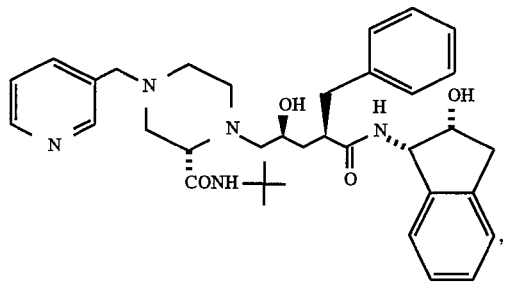

named N-(2(R)-hydroxy-1(S)-indanyl)-2(R)-phenylmethyl-4(S)-hydroxy-5-(1-(4-(3-pyridylmethyl)-2(S)-N'-(t-butylcarbamoyl)-piperazinyl ))-pentaneamide, or pharmaceutically acceptable salt thereof, which is synthesized by the methods of EP 0541168.

Compound D is

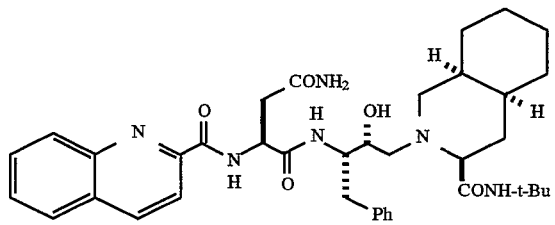

or pharmaceutically acceptable salt thereof. It is synthesized by the procedures of EP 0346847. See also N. A. Roberts et al., *Science* 248, 358 (1990).

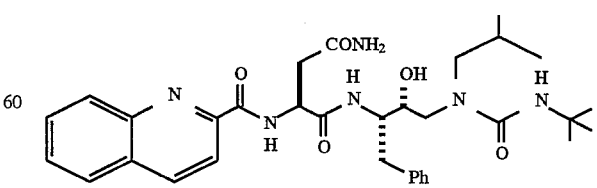

It is synthesized by the procedure of EP 0346847, PCT WO 92/08700 and PCT WO 92/8698.

Compound F is:

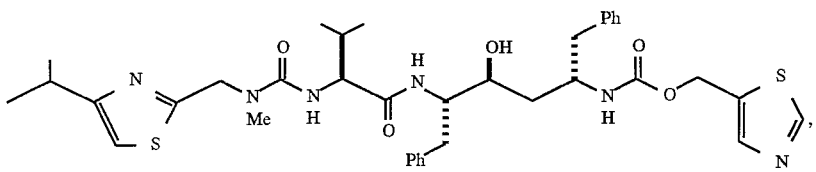

or pharmaceutically acceptable salt thereof. It is synthesized by the method of EP 0486948.

Preferred combinations are simultaneous or alternating treatments of an inhibitor of HIV protease and a non-nucleoside inhibitor of HIV reverse transcriptase. An optional third component in the combination is a nucleoside inhibitor of HIV reverse transcriptase, such as AZT, ddC or ddI. A preferred inhibitor of HIV protease is Compound A. Preferred non-nucleoside inhibitors of HIV reverse transcriptase include Compound B, Compound C or nevirapine. These combinations may have synergistic effects on limiting the spread of HIV. Preferred combinations include the following (1) Compound A, with a preferred non-nucleoside inhibitor of HIV reverse transcriptase, and, optionally, AZT or ddI or ddC; (2) Compound A, and any of AZT or ddI or ddC.

Another preferred set of combinations are simultaneous or alternating treatments of an inhibitor of HIV protease of this invention, with any one or more of efficacious inhibitors of HIV protease. An optional third component in the combination is a nucleoside inhibitor of HIV reverse transcriptase, such as AZT, ddC or ddI. A preferred inhibitor of this invention is Compound A. Preferred efficacious inhibitors of HIV protease include Compound J, Compound D, Compound E or Compound F. These combinations may have synergistic effects on limiting the spread of HIV. Preferred combinations include a combination comprising a compound of this invention, and an inhibitor of HIV protease selected from Compounds J, D, E and F.

Assay for Inhibition of Microbial Expressed HIV Protease

Inhibition studies of the reaction of the protease expressed in Eschericia coli with a peptide substrate [Val-Ser-Gln-Asn-(betanaphyl)Ala-Pro-Ile-Val, 0.5 mg/mL at the time the reaction is initiated] were in 50 mM Na acetate, pH 5.5, at 30° C. for 1 hour. Various concentrations of inhibitor in 1.0 ml DMSO were added to 25 ml of the peptide solution in water. The reaction is initiated by the addition of 15 ml of 0.33 nM protease (0.11 ng) in a solution of 0.133M Na acetate pH 5.5 and 0.1% bovine serum albumin. The reaction was quenched with 160 ml of 5% phosphoric acid. Products of the reaction were separated by HPLC (VYDAC wide pore 5 cm C-18 reverse phase, acetonitrile gradient, 0.1% phosphoric acid). The extent of inhibition of the reaction was determined from the peak heights of the products. HPLC of the products, independently synthesized, proved quantitation standards and confirmation of the product composition. Compound A showed $IC_{50}$ values of about 1.2 nM.

CELL SPREAD ASSAY

Inhibition of the spread of HIV in cell culture was measured according to Nunberg, J. H. et al., *J. Virol.* 65, 4887 (1991). In this assay, MT-4 T-lymphoid cells were infected with HIV-1 (wild-type, unless otherwise indicated) by using a predetermined inoculum, and cultures were incubated for 24 h. At this time, ≦1% of the cells were positive by indirect immunofluorescence. Cells were then extensively washed and distributed into 96-well culture dishes. Serial twofold dilutions of inhibitor were added to the wells, and cultures were continued for 3 additional days. At 4 days postinfection, 100% of the cells in control cultures were infected. HIV-1 p24 accumulation was directly correlated with virus spread. The cell culture inhibitory concentration was defined as the inhibitor concentration in nanomoles/liter which reduced the spread of infection by at least 95%, or $CIC_{95}$. The $CIC_{95}$ for compound A is 25 nM.

INHIBITION OF VIRUS SPREAD

A. Preparation of HIV-infected MT-4 cell Suspension

MT cells were infected at Day 0 at a concentration of 250,000 per ml with a 1:1000 dilution of HIV-1 strain IIIb stock (final 125 pg p24/ml; sufficient to yield<1% infected cells on day 1 and 25–100% on day 4). Cells were infected and grown in the following medium: RPMI 1640 (Whittaker BioProducts), 10% inactivated fetal bovine serum, 4 mM glutamine (Gibco Labs) and 1:100 Penicillin-Streptomycin (Gibco Labs).

The mixture was incubated overnight at 37° C. in 5% $CO_2$ atmosphere.

B. Treatment with Inhibitors

A matrix of nanomolar range concentrations of the pairwise combinations is prepared. At Day 1, aliquots of 125 ml of inhibitors are added to equal volumes of HIV-infected MT-4 cells (50,000 per well) in a 96-well microtiter cell culture plate. Incubation is continued for 3 days at 37° C. in 5% $CO_2$ atmosphere.

C. Measurement of Virus Spread

Using a multichannel pipettor, the settled cells are resuspended and 125 ml harvested into a separate microtiter plate. The supernatant is assayed for HIV p24 antigen.

The concentration of HIV p24 antigen is measured by an enzyme immunoassay, described as follows. Aliquots of p24 antigen to be measured are added to microwells coated with a monoclonal antibody specific for HIV core antigen. The microwells are washed at this point, and at other appropriate steps that follow. Biotinylated HIV-specific antibody is then added, followed by conjugated streptavidin-horseradish peroxidase. A color reaction occurs from the added hydrogen peroxide and tetramethylbenzidine substrate. Color intensity is proportional to the concentration of HIV p24 antigen.

Calculation of Degree of Synergy

When there is synergy pairwise combinations of inhibitors are found to exhibit markedly enhanced inhibition of virus spread, in comparison to each inhibitor alone, or in comparison to merely additive inhibition of each inhibitor.

The data is processed as follows: fractional inhibitory concentration ratios (FIC) are calculated according to Elion, et al., *J. Biol. Chem.*, 208,477 (1954). The minimum sum of FICS, which is the maximum synergy, is determined for various pairwise combinations. The smaller the number, the greater the synergy.

EXAMPLE 1

Preparation of 3(S)-azido-(1,2R)-epoxy-4-phenylbutane, Compound 9

A quantity of CuCN, 2.43 g, was added to a solution of butadiene monooxide, 19 g, in 500 mL anhydrous tetrahydrofuran and the mixture was cooled to −78° C. Phenyl magnesium bromide solution in ether, 32 mmol, was added dropwise to this mixture. The reaction mixture was warmed to 0° C. and was stirred until the reaction became homogeneous. The reaction mixture was cooled to −78° C. and 0.29 mole of phenylmagnesium bromide solution in ether was added dropwise for 30 min. The reaction mixture was allowed to warm to room temperature with stirring then quenched by slow addition of saturated $NH_4Cl$ (50 mL) followed by $NH_4OH$ (30 mL), saturated $NH_4Cl$ (200 mL) and $H_2O$ (100 mL). Aqueous layer was extracted with two 200 mL portions of ethyl acetate. Combined organic layers were dried and concentrated. The residue was distilled under vacuum (0.1 torr) at 100° C. to give trans-4-phenyl-2-butene-1-ol (38.9 g, 79% pure).

A mixture of powdered 4 Å molecular sieves, 3 g, titanium tetraisopropoxide, 1.5 mL, and diethyl D-tartrate, 1.1 mL, in anhydrous methylene chloride (350 mL) was cooled to −20° C. and tert-butylhydroperoxide solution in isooctane, 210 mmol, was added slowly with stirring. After 30 minutes at −20° C. a solution of trans-4-phenyl-2-butene-1-ol, 15.3 g, in anhydrous methylene chloride (50 mL) was added dropwise for 20 min at −20° C. The reaction mixture was aged at −20° C. in a freezer for 20 hours. Water (40 mL) was added to the reaction mixture and after 30 minutes at 0° C., 30% NaOH in brine (6 mL) was added. The resulting mixture was stirred for 1 h at room temperature. The organic phase was separated and the aqueous layer was extracted with two 30 mL portions of methylene chloride. Combined organic layers were dried over $Na_2SO_4$, diluted with toluene (300 mL) and concentrated. Chromatography on silica gel with 40% ethyl acetate in hexane gave (2R, 3R)-epoxy-4-phenylbutan-1-ol, compound 7 (10.3 g).

A solution of titanium tetraisopropoxide, 5.6 mL, and azidotrimethylsilane, 5.0 mL, in anhydrous benzene (100 mL) was refluxed for 5 h. To this refluxing mixture was added a solution of compound 7, 2.6 g, in anhydrous benzene (10 mL). The reaction mixture was refluxed for 15 min, cooled to room temperature and quenched by addition of 5% $H_2SO_4$ (150 mL). After stirring the resulting biphasic mixture for 1 h, the organic layer was separated and the aqueous layer was extracted with two 20 mL portions of ethyl acetate. Combined organic layers were washed with saturated sodium bicarbonate (50 mL), dried over $MgSO_4$ and concentrated. The oily azidodiol product was dissolved in chloroform (30 mL) and 2-acetoxy-isobutyryl chloride, 2.5 mL, was added. After stirring for 5 h at room temperature, saturated sodium bicarbonate (50 mL) was added and the resulting biphasic mixture was stirred for 10 min. The aqueous layer was extracted with two 30 mL portions of chloroform. Combined organic layers were dried over $Na_2SO_4$ and concentrated. The residue was dissolved in anhydrous tetrahydrofuran (10 mL) and solid NaOMe, 0.614 g, was added. After stirring for 3 h at room temperature, saturated $NH_4Cl$ (20 mL) was added and the mixture extracted with two 20 mL portions of ethyl acetate. Combined organic layers were dried over $MgSO_4$ and concentrated. Chromatography on silica gel with 8% ethyl acetate in hexanes gave 3(S)-azido-(1, 2R)-epoxy-4-phenylbutane (1.32 g) as an oil.

EXAMPLE 2

Preparation of 2(R,S)-(methylethyl)-3(R,S)-hydroxytetrahydrothiophene, Compound 13

Ethyl 3-mercaptopropionate (22.46 g) was dissolved in absolute ethanol (60 mL) and the solution was cooled to −20° C. To it was added sodium ethoxide solution in ethanol (62.5 mL of 21%). A solution of ethyl 2-bromoisovalerate (35 g) in absolute ethanol (60 mL) was added slowly. The reaction mixture was stirred for 2 hours while the reaction temperature was allowed to warm to room temperature. Saturated $NH_4Cl$ (150 mL) was added to the reaction mixture and organic layer was separated. The aqueous layer was extracted with ethyl acetate (100 mL×3). The combined organic layers were dried over $Na_2SO_4$ and concentrated. Sodium (0.88 g) was dissolved in absolute ethanol (40 mL) at 0° C. and the solution was concentrated. The residue was dissolved in toluene and the product from the previous reaction, Compound 10, (7.78 g) was added. The reaction mixture was heated to reflux for 2 hours. The reaction mixture was cooled to room temperature and 1N HCl was added to the reaction mixture until the pH became acidic. The crude product was extracted with EtOAc (50 mL×3) and the combined organic layers were washed with brine, were dried over $Na_2SO_4$ and concentrated. The residue, Compound 11, was heated with 10% $H_2SO_4$ (40 mL) at 100° C. overnight. The crude product was extracted with ethyl acetate (50 mL×3). The combined organic layers were dried over $Na_2SO_4$ and concentrated. The residue (2(S,R)-(methylethyl)-tetrahydrothiophen-3-one), compound 12, was dissolved in methylene chloride (60 mL) and the solution was cooled to 0° C. Diisobutylaluminumhydride (25 mL, 1M) in methylene chloride was added dropwise. The reaction mixture was stirred for one hour at 0° C. The reaction was quenched by the dropwise addition of water until no gas evolved. 1N HCl (50 mL) was added and the crude product was extracted with methylene chloride (50 mL×3). Combined organic layers were washed with saturated $NaHCO_3$, brine and dried over $Na_2SO_4$. Concentration and purification by column chromatography, eluting with 20% ethyl acetate in hexane gave Compound 13, as an oil (1.72 g):

$^1H$ NMR ($CDCl_3$): 4.36 (br, s, 1H), 3.1–2.85 (m, 3H), 2.23 (dd, J=6.8 Hz, 13.3 Hz, 1H), 1.95–1.77 (m, 3H), 1.07 (d, J=6.5 Hz, 3H), 1.02 (d, J=6.7 Hz, 3H).

EXAMPLE 3

Preparation of 3(R,S)-[2(R,S)-methylethyl] tetrahydrothienyl succinimidyl carbonate, Compound 14

A mixture of 1.52 g (10.4 mmol) of 2(R,S)-methylethyl-3(R,S)-hydroxytetrahydrothiophene, 2.93 g (11.4 mmol) of N,N'-disuccinimidyl carbonate and 1.16 g (11.4 mmol) of triethylamine was dissolved in 25 mL of acetonitrile and stirred for 18 hours. The solvent was removed in vacuo and the resulting mixture partitioned between 100 mL of EtOAc and water (1:1). The aqueous layer was separated and washed with water (2×50 mL), brine (1×60 mL), dried, filtered, and the solvent removed. The resulting solid was dissolved in 100 mL EtOAc/hexane (1:1) and passed through a 3" silica gel pad. The pad was washed with an additional 1 L of EtOAc/hexane and the solvent removed to give 2.8 g (93%) of the desired carbonate.

EXAMPLE 4

Preparation of N-tert-butyl-1-[3(S)-azido-2(R)-hydroxy-4-phenylbutyl]-4-(1,1-dimethylethoxycarbonyl)piperazine-2(S)-carboxamide, Compound 17

A mixture of 22.4 g (80 mmol) of N-t-butyl-4-(1,1-dimethylethoxycarbonyl)piperazine-2(S)-carboxamide (product of Example 12) and 15 g (80 mmol) of 3(S)-azido-(1,2R)-epoxy-4-phenylbutane (product of Example 1) in 200 mL of isopropanol was heated to 80° C. for 18 hours. Subsequent removal of the solvent under reduced pressure gave 23 g (50 mmol) of the desired product as a resin which was used without further purification in the next step.

Alternatively, a mixture of 0.063 g (0.2 mmol) N-tert-butyl-4-(1,1-dimethylethoxycarbonyl)piperazine-2(S)-carboxamide and 1.6 g (22 mmol) $Al_2O_3$ in 50 mL $Et_2O$ was stirred for 30 min, after which 0.038 g (0.2 mmol) 3(S)-azido-(1,2(R))-epoxy-4-phenylbutane was added. Stirring was continued for 18 hours, after which the solid was filtered and washed with 50 mL of $Et_2O$. The filtrate was concentrated to dryness and the residue was purified by preparative thin layer chromatography (5% methanol in methylene chloride) to give 0.055 g (0.012 mmol) of the desired product as a resin in 59% yield.

EXAMPLE 5

Preparation of N-tert-butyl-1-[2'(R)-hydroxy-4'-phenyl-3'(S)-[3"(R)-[2'"(R)-methylethyl]tetrahydrothienyloxycarbonylamino]butyl]-4-(1,1-dimethylethoxycarbonyl)piperazine-2(S)-carboxamide, Compound 19

A mixture of 23 g N-tert-butyl-1-[3(S)-azido-2(R)-hydroxy-4-phenylbutyl]-4-(1,1-dimethylethoxycarbonyl)piperazine-2(S)-carboxamide and 2 g of $Pd(OH)_2/C$ in 100 mL ethanol was shaken under a hydrogen atmosphere at ambient pressure for 18 hours. The solid was filtered through a Celite pad and washed with 50 mL of ethanol. The solvent was removed under reduced pressure and the residue partitioned between 200 mL ethyl acetate/water (1:1). The aqueous layer was separated and washed with EtOAc (1×20 mL). The combined organic layer was washed with water (2×50 mL) and brine (1×60 mL), dried, and the solvent removed to yield 19 g of crude amine which (Compound 18) which was used without further purification.

To a stirred solution of 0.100 g (0.23 mmol) of N-tert-butyl-1-[3(S)-amino-2(R)-hydroxy-4-phenylbutyl]-4-(1,1-dimethyl-ethoxycarbonyl)piperazine-2(S)-carboxamide (Compound 18) and 0.066 g (0.023 mmol) of 3(R,S)-[2(R,S)-methylethyl]-tetrahydro-thienyl succinimidyl carbonate (product of Example 4) in 2 mL of methylene chloride was added 0.023 g (0.032 mL, 0.23 mmol) of triethylamine and the stirring was continued for 15 hours at ambient temperature. The mixture was partitioned between water (5 mL) and methylene chloride (5 mL) and the aqueous layer was extracted with methylene chloride (3×5 mL). Combined organic layer was washed with water (5 mL) and brine (5 mL) and dried over anhyd. $Na_2SO_4$. Removal of solvent in vacuo followed by preparative thin layer chromatography (silica gel, 20×20 cm, 1 mm, 5% $MeOH/CH_2Cl_2$) provided 0.101 g (71% yield) of a diastereomeric mixture as a gummy residue. UV(lmax)=256 nm;

$^1$H NMR ($CDCl_3$): 7.18–7.30 (5H, m), 6.20 (1H, br s), 5.24 (1H, d, J=9 Hz), 4.94 (1H, m), 1.6–4.0 (20H), 1.44 (9H, s), 1.35 (9H, s), 0.96 (3/2H, d, J=7 Hz), 0.95 (3/2H, d, J=7 Hz), 0.93 (3/2H, d, J=7 Hz), 0.86 (3/2H, d J=7 Hz).

EXAMPLE 6

Preparation of N-tert-butyl-1-[2'(R)-hydroxy-4'-phenyl-3'(S)-[3"(R)-[1'",1'",1'"-dioxo-2'"(R)-methylethyl]tetrahydrothienyloxycarbonylamino]-butyl]-4-(1',1'-dimethylethoxycarbonyl)piperazine-2(S)-carboxamide To a stirred solution of 50 mg (0.08 mmol) of a 1:1 mixture of N-tert-butyl-1-[2'(R)-hydroxy-4'-phenyl-3'(S)-[3"(R)-[2'"(R)-methylethyl]tetrahydrothienyloxycarbonylamino]butyl]-4(1',1'-dimethylethoxycarbonyl)piperazine-2(S)-carboxamide and N-tert-butyl-1-[2'(R)-hydroxy- 4'-phenyl-3'(S)-[3"(S)-[2'"(S)-methylethyl]-tetrahydrothienyloxy-carbonylamino]butyl]-4-(1',1'-dimethylethoxy-carbonyl)piperazine-2(S)-carboxamide, 28 mg (0.24 mmol) of N-methylmorpholine N-oxide were stirred in 0.5 mL 10:1 acetone water was added 0.1 ml $OsO_4$ solution in t-butanol (2.5%). After stirring 18 hours, 0.5 g sodium metabisulfite was added and stirring was continued for 30 min. The solid was filtered and the solvent removed. The residue was partitioned between 50 mL 1:1 EtOAc/water, the organic layer separated and the aqueous washed with EtOAc (2×20 mL). The combined organics were then washed with water (3×25 mL), brine (1×30 mL), dried, and the solvent removed. Medium pressure silica gel liquid chromatography (1:1 hexane/EtOAc) of the residue yielded 19.2 mg of N-tert-butyl-1-[2'(R)-hydroxy-4'-phenyl-3'(S)-[3"(R)-[1'",1'"-dioxo-2'"(R)-methylethyl]tetrahydrothienyloxycarbonyl-amino]butyl]-4-(1',1'-dimethylethoxycarbonyl)piperazine-2(S)-carboxamide, the desired compound, as the first fraction and 19.5 mg of N-tert-butyl-1-[2'(R)-hydroxy-4'-phenyl-3'(S)-[3"(S)-[1'", 1'"-dioxo-2'"(S)-methylethyl]tetrahydrothienyloxycarbonylamino]butyl]-4-(1',1'-dimethylethoxycarbonyl) piperazine-2(S)-carboxamide as the second fraction. UV (lmax)=258 nm, $^1$H NMR ($CDCl_3$) 7.14–7.35 (5H, m), 6.17 (1H, m), 5.26 (2H, m), 3.94 (1H, m), 3.83 (1H, m), 3.71 (1H, m), 3.24–3.64 (3H, m), 2.30–3.24 (9H, m), 2.17 (1H, m), 1.96 (1H, m), 1.07–1.80 (5H, m), 1.47 (9H, s), 1.31 (9H, s), 1.15 (3H, d, J=10 Hz), 0.94 (3H, d, J=10 Hz).

Elemental Analysis, calc'd for $C_{32}H_{52}N_4O_8S \times 0.55$ $CH_3COOC_2H_5 + 0.65$ $CH_2Cl_2$ (M.W.=756.526): C,55.33; H, 7.69; N, 7.41 Found: C, 55.38; H, 7.45; N, 7.40

EXAMPLE 7

Preparation of N-tert-butyl-1-[2'(R)-hydroxy-4'-phenyl-3'(S)-[3"(R)-[1'",1'"-dioxo-2'"(R)-methylethyl]tetrahydrothienyloxy-carbonyl-amino]butyl]piperazine-2(S)-carboxamide, Compound 20

HCl gas was bubbled through a stirred solution of 1 g of N-tert-butyl-1-[2'(R)-hydroxy-4'-phenyl-3'(S)-[3"(R)-[1'", 1'"-dioxo-2'"(R)-methylethyl]tetrahydrothienyloxycarbonylamino]butyl]-4-(1',1'-dimethylethoxycarbonyl)piperazine-2(S)-carboxamide in 50 mL EtOAc at 0° C. for 10 min., after which the gas flow was stopped and the reaction mixture allowed to stir for an additional 15 min. The solvent was removed under reduced pressure and the residue treated with 50 mL $CHCl_3$ which had been previously saturated with $NH_3$ gas. The resulting slurry was filtered and the solvent removed in vacuo to give 0.8 g N-tert-butyl-1-[2'(R)-hydroxy-4'-phenyl-3'(S)-[3"(R)-[1'",1'"-dioxo-2'"(R)-methylethyl]tetrahydro-thienyloxycarbonylamino]butyl]-piperazine-2(S)-carboxamide as a resin.

EXAMPLE 8

Preparation of N-tert-butyl-1-[2'(R)-hydroxy-4'-phenyl-3'(S)-[3"(R)-[1''',1'''-dioxo-2'''(R)-methylethyl]tetrahydrothienyloxycarbonylamino]butyl-]-4-[(3'-methoxy-4',5'-methylenedioxyphenyl)methyl]piperazine-2(S)-carboxamide To a mixture of N-tert-butyl-1-[2'(R)-hydroxy-4'-phenyl-3'(S)-[3"(R)-[1''',1'''-dioxo-2'''(R)-methylethyl]tetrahydrothienyl-oxycarbonylamino]butyl]piperazine-2(S)-carboxamide (1.258 g, 2.277 mmol, Example 11) and 3-methoxy-4,5-methylenedioxybenzaldehyde (0.821 g, 4.559 mmol, Lancaster) in 20 mL 1,2-dichloroethane were added Na(OAc)₃BH (0.728 g, 3.434 mmol), and acetic acid (0.17 mL, 0.457 mmol). The mixture was stirred 18 h at room temperature. It was diluted with EtOAc (50 mL) and washed with sat aq NaHCO₃ (2×50 mL), water (2×20 mL), and brine (50 mL). The organic layer was dried over anhyd Na₂SO₄, filtered and the filtrate was concentrated under reduced pressure. The crude product was purified on a chromatographic column (silica gel, eluted with 1% MeOH/CHCl₃) to yield 1.108 g (68% yield) of the desired product as a white solid. mp 102°–105° C.; UV(lmax) 247 nm;

¹H NMR (CDCl₃) 8.22 (1H, br s), 7.14–7.27 (5H, m), 6.46 (1H, s), 6.41 (1H, s), 5.96 (2H, br s), 5.38 (1H, d, J=9.9 Hz), 5.30 (1H, s), 5.24 (1H, m), 4.78 (1H, m), 3.93 (1H, m), 3.90 (3H, s), 3.84 (1H, m), 3.38 (1H, d, $J_{AB}$=12.8 Hz), 3.34 (1H, d, J=12.8 Hz), 3.07 (1H, dd, J=12.8, 7.9 Hz), 2.95 (1H, dd, J=9.2, 4.4 Hz), 2.94 (1H, m), 2.90 (1H, dd, J=13.4, 4.6 Hz), 2.83 (1H, dd, J=13.6, 4.4 Hz), 2.78 (1H, m), 2.72 (1H, m), 2.62 (1H, m), 2.41 (1H, dd, J=11.5, 3.1 Hz), 2.25 (1H, m), 2.18 (1H, m), 1.86–2.02 (3H, m), 1.38 (9H, s), 1.16 (3H, d, J=6.4 Hz), 0.92 (3H, d, J=6.8 Hz); LRFABMS: 717; HRFABMS calc'd for C₃₆H₅₃N₄O₉S: 717.3533, obsd: 717.3538;

Elemental Analysis calc'd for C₃₆H₅₂N₄O₉S×0.55 H₂O C, 59.49; H, 7.36; N, 7.71 Found: C, 59.47; H, 7.23; N, 7.69

EXAMPLE 9

Employing substantially the same procedure as described in Example 10, but treating the N-tert-butyl-1-[2'(R)-hydroxy-4'-phenyl-3'(S)-[3"(R)-[1''',1'''-dioxo-2'''(R)-methylethyl]tetrahydrothienyl-oxycarbonylamino]butyl]piperazine-2(S)-carboxamide used therein (Compound (i) below) with the aldehyde agent (ii) indicated below in place of the 3-methoxy-4,5-methylenedioxybenzaldehyde used, the following products defined by Formula (iii) were made:

EXAMPLE 10

Preparation of N-tert-butyl-1-[2'(R)-hydroxy-4'-phenyl-3'(S)-[3"(R)-[1''',1'''-dioxo-2'''(R)-methylethyl]tetrahydrothienyloxycarbonylamino]-butyl]-4-[3-(furo[2,3-b])pyridylmethyl]piperazine-2(S)-carboxamide Step 1: Preparation of Furo[2,3-b]pyridine-2,5-dicarboxylic acid

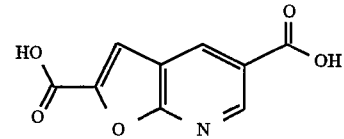

To solution of the known [Snyder, H. R., Ebetino, F. F. *J. Het. Chem.* 3, 202–205 (1966)]diethyl furo[2,3-b]pyridine-2,5-dicarboxylate (1.22 g, 4.923 mmol) in 10 mL of 95% ethanol was added a solution of potassium hydroxide (0.66 g, 11.81 mmol) dissolved in 10 mL of water. The reaction was warmed to 80° C. for 3 h, cooled to RT and filtered. The bispotassium salt was dissolved in water and acidified with 10% HCl to pH 2. This solution was filtered and dried under vacuum to afford 850 mg of a white solid.

1H NMR (400 MHz, (CD₃)₂SO) δ8.98 (d, J=2.2 Hz, 1H), 8.76 (d, J=2.2 Hz, 1H), 7.69 (s, 1H), 4.25 (br s, 3H).

Step 2: Preparation of Furo[2,3-b]pyridine-5-carboxylic acid

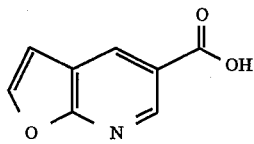

To a suspension of furo[2,3-b]pyridine-2,5-dicarboxylic acid (0.36 g, 1.484 mmol) in 3 mL of quinoline, under Ar, was added Cu powder (180 mg, 2.82 mmol) and warmed to 210° C. for 1.5 h. The reaction was cooled to RT and diluted with 50 mL of methylene chloride and filtered through Celite. The organic layer was extracted with sat'd Na₂CO₃ (2×40 mL), acidified to pH 3 with 3N HCl, and filtered to afford 80 mg of a tan solid. The aqueous layer was extracted with ether/methanol (85/15) (3×50 mL) and washed with brine (1×10 mL), dried over MgSO₄, filtered and concentrated to afford an additional 35 mg of product.

1H NMR (400 MHz, (CD₃OD) δ8.89 (s, 1H), 8.67 (d, J=2.0 Hz, 1H), 7.97 (d, J=2.5 Hz, 1H), 7.01 (d, J=2.4 Hz, 1H).

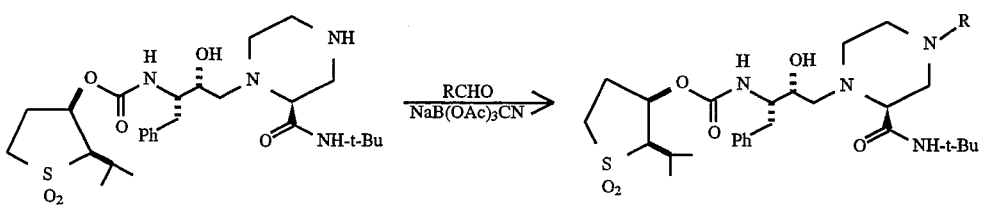

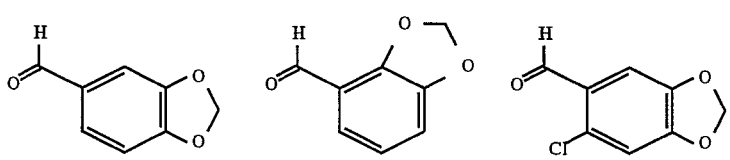

ii

Step 3: Preparation of methyl furo[2,3-b]pyridine-5-carboxylate

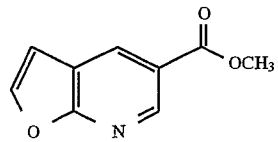

To furo[2,3-b]pyridine-5-carboxylic acid (3.0 g, 18.40 mmol) dissolved in 40 mL of methanol was added 160 mL of chloroform and then trimethysilyldiazomethane (42 mL, 10% solution in hexanes) slowly. After 0.5 h 4 drops glacial acetic acid was added and the reaction mixture was concentrated. This provided 3.20 g as an off white solid.

1H NMR (400 MHz, CDCl$_3$) δ9.02 (d, J=2.0 Hz, 1H), 8.60 (d, J=2.0 Hz, 1H), 7.79 (d, J=2.5 Hz, 1H), 6.87 (d, J=2.5 Hz, 1H), 3.98 (s, 3H).

Step 4: Preparation of 5-hydroxymethyl furo[2,3-b]pyridine

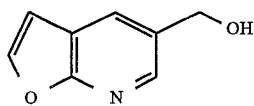

A flame dried 500 mL round bottom flask was charged with methyl furo[2,3-b]pyridine-5-carboxylate (3.20 g, 18.08 mmol) dissolved in 90 mL of THF and cooled to 0° C. To this was added diisobutylaluminum hydride (46 mL, 46.1 mmol, 1M solution in hexanes) over 10 minutes and the cooling bath removed. After 4 h the reaction mixture was cooled to 0° C. and slowly quenched with rochelle salts (100 mL). After an additional 18 h the layers were separated and the aqueous layer was extracted with ethyl acetate (4×40 mL). The combined organic layers were washed with brine (1×20 mL), dried over MgSO$_4$, filtered and concentrated. The residue was purified via flash column chromatography (40×150 mm column, gradient elution CH$_2$Cl$_2$: CH$_2$Cl$_2$ sat'd with NH$_3$: MeOH 60:39:1.0 (1000 mL), 60:38:2 (1000 mL), 60:37:3 (1000 mL), 60:36:4 (1000 mL). This provided 2.16 g of a white solid.

$^1$H NMR (400 MHz, CDCl$_3$) δ8.19 (d,J=2.0 Hz, 1H), 7.92 (d,J=2.0 Hz, 1H), 7.64 (d, J=2.5 Hz, 1H), 6.69 (d, J=2.4 Hz, 1H), 4.78 (d, J=3.8 Hz, 2H), 4.69 (br s, 1H).

Step 5: Preparation of 3-chloromethyl furo[2,3-b]pyridine hydrochloride

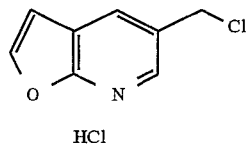

HCl

To a solution of 5-hydroxymethyl furo[2,3-b]pyridine dissolved in 9 mL of methylene chloride cooled to 0° C. was added thionyl chloride (4.23 mL, 57.99 mmol). The ice bath was removed and after 1 h the reaction mixture was concentrated to afford 2.86 g of an off white solid.

H MNR (400 MHz, CDCl$_3$) δ8.40 (d, J=2.0 Hz, 1H), 8.13 (d, J=2.2 Hz, 1H), 7.80 (d, J=2.4 Hz, 1H), 6.86 (d, J=2.4 Hz, 1H), 4.74 (s, 2H).

Step 6: Preparation of N-tert-butyl-1-[2'(R)-hydroxy-4'-phenyl-3'(S)-[3"(R)-[1'",1'"-dioxo-2'"(R)-methylethyl] tetrahydro-thienyloxycarbonylamino]-butyl]-4-[4'-(3-furo [2,3-b]pyridylmethyl]piperazine-2(S)-carboxamide A mixture of N-tert-butyl-1-[2'(R)-hydroxy-4'-phenyl-3' (S)-[3"(R)-[1'",1'"-dioxo-2'"(R)-methylethyl] tetrahydrothienyl-oxycarbonylamino]butyl]piperazine-2(S)-carboxamide (0.169 g), 3-chloromethyl furo[2,3-b]pyridine hydrochloride (0.050 g), and triethylamine (0.630 mL) in DMF (1 mL) was stirred for 18 h. The mixture was diluted with 25 mL of EtOAc and washed with water (3×12 mL), brine (1×10 mL), dried over anhyd MgSO$_4$, filtered and concentrated under reduced pressure. The residue was purified by silica gel column chromatography (eluted with NH$_3$ saturated chloroform) to give 144 mg (69% yield) of white solid after removal of residual DMF. m.p. 120°–130° C.; UV (lmax) 201 nm;

1H NMR (CDCl$_3$): 8.26 (1H, d, J=1.8 Hz), 8.07 (1H, br s), 7.85 (1H, d, J=1.5 Hz), 7.75 (1H, d, J=2.4 Hz), 7.16–7.26 (5H, m), 6.76 (1H, d, J=2.4 Hz), 5.25 (1H, d, J=9.7 Hz), 5.24 (1H, m), 4.68 (1H, br s), 3.92 (1H, m), 3.85 (1H, m), 3.63 (1H, d, J$_{AB}$=12.8 Hz), 3.58 (1H, d, J$_{AB}$=12.8 Hz), 3.39 (1H, br s), 3.08 (1H, dd, J=12.6, 7.7 Hz), 2.89–2.97 (3H, m), 2.71–2.84 (3H, m), 2.61–2.65 (2H, m), 2.51 (1H, dd, J=11.7, 3.3 Hz), 2.34 (1H, m), 2.18 (1H, m), 1.88–2.02 (3H, m), 1.36 (9H, s), 1.17 (3H, d, J=6.4 Hz), 0.92 (1H, d, J=6.8 Hz), 2.62 (1H, m), 2.41 (1H, dd, J=11.5, 3.1 Hz), 2.25 (1H, m), 2.18 (1H, m), 1.86–2.02 (3H, m), 1.38 (9H, s), 1.16 (3H, d, J=6.4 Hz), 0.92 (3H, d, J=6.8 Hz) Elemental analysis calculated for C$_{35}$H$_{49}$N$_5$O$_7$S+0.40 EtOAc (719.11): C, 61.13; H, 7.32; N, 9.74 Found: C, 61.41; H, 7.48; N, 9.74

EXAMPLE 11

Employing substantially the same procedure as described in Example 11, but treating the N-tert-butyl-1-[2'(R)-hydroxy-4'-phenyl-3'(S)-[3"(R)-[1'",1'"-dioxo-2'"(R)-methylethyl]tetrahydrothienyl-oxycarbonylamino]butyl] piperazine-2(S)-carboxamide used therein (Compound (i) below) with the alkylating agent (R'-X) indicated below in place of the 3-chloromethyl furo[2,3-b]pyridine hydrochloride used, the following products defined by Formula (iii) were made:

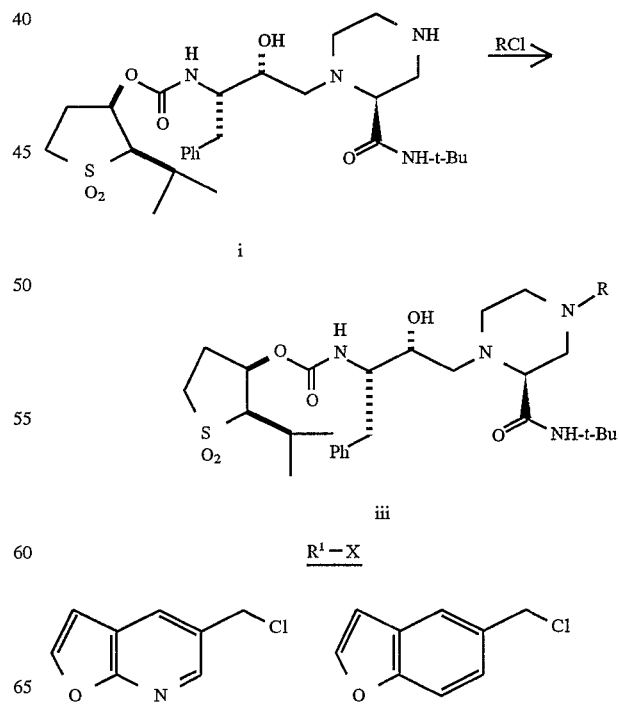

i iii

R$^1$—X

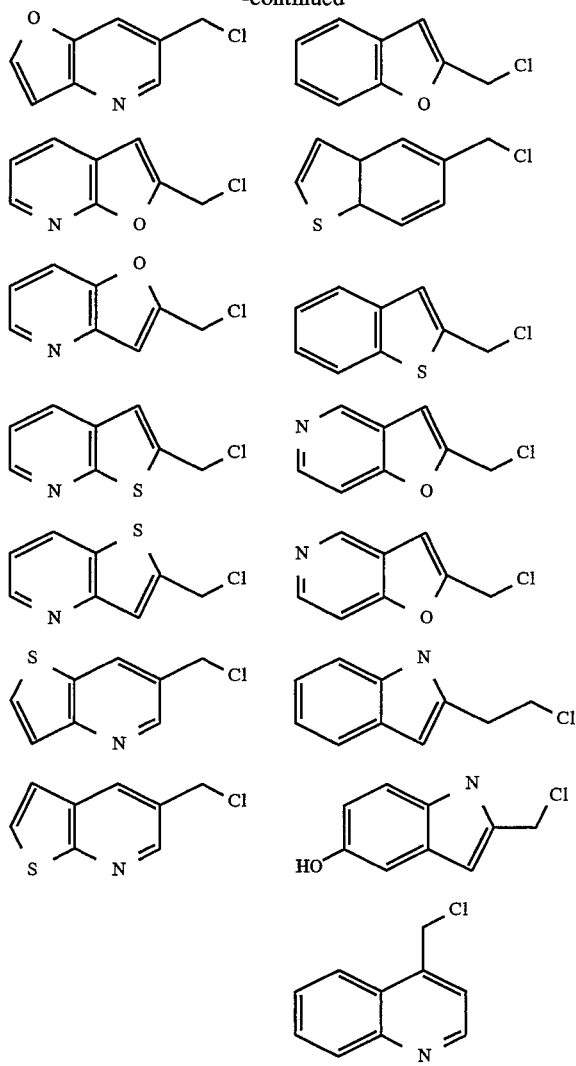

EXAMPLE 12

Preparation of N-t-butyl-4-(1,1-dimethylethoxycarbonyl)-piperazine-2(S)-carboxamide, Compound 4

Step 1: Preparation of 4-(1,1-dimethylethoxycarbonyl)-1-(phenylmethoxycarbonyl)-piperazine-2(S)-carboxamide The title compound was prepared following the procedure of Bigge, C. F. et al., *Tetrahedron Lett*, 30, 5193 (1989); starting with 2(S)-piperazinecarboxylic acid. (See also Felder, E. et al., *Helv. Chim. Acta* 117, 888 (1960)).

Step 2: Preparation of N-t-butyl-4-(1,1-dimethylethoxy-carbonyl)-1-(phenylmethoxycarbonyl)-piperazine-2(S)-carboxamide To 9.90 g (27.16 mmol) of 4-(1,1-dimethylethoxy-carbonyl)-1-(phenylmethoxycarbonyl)-piperazine-2(S)-carboxamide dissolved in 75 mL of DMF and cooled to 0° C. were added 5.73 g (29.88 mmol) of EDC, 4.03 g (29.88 mmol) of HOBt, 3.14 mL (29.88 mmol) of t-butylamine, and finally 4.16 mL (29.88 mmol) of triethylamine. The reaction mixture was stirred for 18 hours and the reaction volume was concentrated under reduced pressure. The residue was then diluted with 600 mL of EtOAc and washed with 10% HCl (2×75 mL), saturated NaHCO$_3$ (1×75 mL), water (3×75 mL) and brine (1×50 mL), dried over MgSO$_4$ and concentrated to a solid. This solid was triturated with EtOAc:hexane (1:2) and filtered to provide the title compound as a white solid; mp 134°–135° C.

Step 3: Preparation of N-t-butyl-4-(1,1-dimethylethoxycarbonyl)-piperazine-2(S)-carboxamide To 1.20 g (2.86 mmol) of N-t-butyl-4-(1,1-dimethyl-ethoxy-carbonyl)-1-(phenylmethylcarbonyl)piperazine-2 (S)-carboxamide and 1.1 g (0.086 mmol) of 10% Pd/C was added 15 mL of methanol. The vessel was charged with hydrogen and the reaction stirred for 2 hours, filtered through Celite and washed with ethanol. The solvents were removed in vacuo to provide the title product as a foam.

1H NMR (300 MHz, CDCl$_3$) δ6.65 (br, 1H), 4.10 (m, 1H), 3.81 (br, 1H), 3.21 (dd, J=18 and 7 Hz, 1H), 3.02–2.70 (m, 4H), 2.10–2.0 (br, 1H), 1.50 (s, 9H), 1.41(s, 9H).

What is claimed is:

1. A compound of the formula:

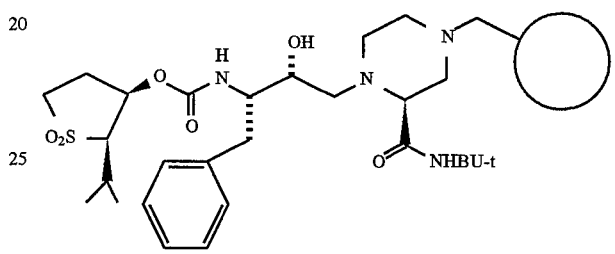

or pharmaceutically acceptable salts thereof, wherein:

 is

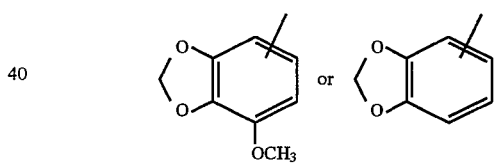

or a pharmaceutically acceptable salt thereof.

2. A compound of the formula

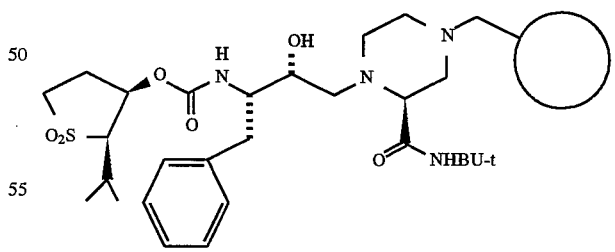

or pharmaceutically acceptable salts thereof, wherein:

 is

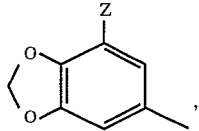

wherein Z is $C_{1-4}$ alkoxy,
or pharmaceutically acceptable salts thereof.

3. A compound of claim 2, which is

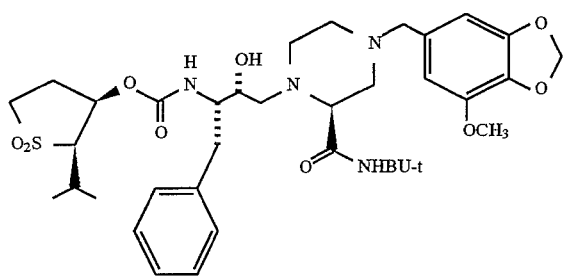

which is N-tert-butyl-1-[2'(R)-hydroxy-4'-phenyl-3'(S)-[3"(R)-[1'",1'"-dioxo-2'"(R)-methylethyl]tetrahydrothienyloxycarbonylamino]butyl]-4-[(3'-methoxy-4',5'-methylenedioxyphenyl)methyl]piperazine-2(S)-carboxamide, or pharmaceutically acceptable salt thereof.

4. A pharmaceutical composition comprising a compound of any of claims 1–3, and a pharmaceutically acceptable carrier.

5. A method of treating AIDS, comprising administering to a mammal in need of such treatment an effective amount of a compound of any of claims 1–3.

6. A method of treating infection by HIV, comprising administering to a mammal in need of such treatment an effective amount of a compound of any of claims 1–3.

* * * * *